United States Patent [19]

Lehmann et al.

[11] 4,356,322
[45] Oct. 26, 1982

[54] PHENOXYALKANOLAMINE DERIVATIVES

[75] Inventors: Dieter Lehmann; Klaus Femmer; Gottfried Faust, all of Radebeul, German Democratic Rep.

[73] Assignee: Veb Arzneimittelwerk Dresden, Radebeul, German Democratic Rep.

[21] Appl. No.: 133,128

[22] Filed: Mar. 24, 1980

Related U.S. Application Data

[63] Continuation-in-part of Ser. No. 963,960, Nov. 27, 1978, abandoned.

[30] Foreign Application Priority Data

Dec. 1, 1977 [DD] German Democratic Rep. ... 202331

[51] Int. Cl.³ ............... C07C 93/06; C07C 91/16
[52] U.S. Cl. .................. 564/185; 564/220; 564/349; 564/350; 564/351
[58] Field of Search ............ 564/351, 350, 349, 185, 564/220

[56] References Cited

U.S. PATENT DOCUMENTS

| | | | |
|---|---|---|---|
| 2,817,675 | 12/1959 | Hofer et al. | 564/349 |
| 3,742,023 | 6/1973 | Koppe et al. | 564/349 |
| 3,864,390 | 2/1975 | LeCount et al. | 564/349 |
| 4,010,280 | 3/1977 | Maruyama et al. | 564/349 |
| 4,041,075 | 8/1977 | Smith | 260/562 |

FOREIGN PATENT DOCUMENTS 1957706  5/1970  Fed. Rep. of Germany.

*Primary Examiner*—Thomas A. Waltz
*Assistant Examiner*—Raymond K. Covington
*Attorney, Agent, or Firm*—Michael J. Striker

[57] ABSTRACT

A series of novel derivatives of phenoxyalkanolamine of the general formula:

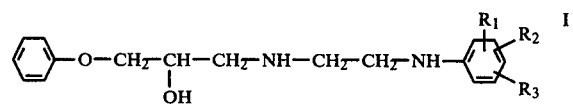

wherein $R_1$, $R_2$ and $R_3$ are the same or different and are hydrogen, alkyl of 1 to 2 carbon atoms, methoxy, halogen, nitro, amino or acylamino residues, and the salts thereof, are described, as are methods for their synthesis. The compounds are highly active $\beta_1$-specific sympathicomimetics with a partially antagonistic component.

20 Claims, No Drawings

PHENOXYALKANOLAMINE DERIVATIVES

CROSS-REFERENCE TO RELATED APPLICATION

The present application is a continuation-in-part application of my copending application Ser. No. 963,960 filed Nov. 27, 1978, and now abandoned.

BACKGROUND OF THE INVENTION

The invention concerns a series of novel derivatives of phenoxyalkanolamine, and methods of preparing them, of the general formula:

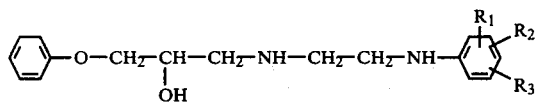

and their salts, wherein the radicals $R_1$, $R_2$ and $R_3$ can be the same or different and are hydrogen, alkyl of 1 to 2 C atoms, methoxy, halogen, nitro, amino or acylamino residues.

The novel compounds produced according to the methods of the invention are highly active $\beta_1$-specific sympathicomimetics with a partially antagonistic component.

The production of structurally-related derivatives of phenoxyalkanolamine has been described in BRD-OS No. 19 57 706. The preferred compounds of this reference are 3-phenoxy-1-phenoxyalkylaminopropanol-(2)-derivatives, in which the phenyl group of the 1-phenoxyalkylamino group carries an electron-withdrawing polar substituent, and in which the 3-phenoxy moiety is preferably substituted by alkyl radicals. From this range of compounds, those in which the polar substituent is a carbamoyl group are selected as of a particularly great efficacy. The level of efficacy is determined by measuring the blocking action on $\beta$-adrenergic receptors of the 3-phenoxy-1-phenoxyalkylaminopropanol-(2)-derivatives, and the degree of attenuation of catecholamine activity in the nervous system. The compound described in BRD-OS No. 19 57 706, as emphasized in that reference, are $\beta$-receptor blocking agents.

As reported by M. J. Davey in Arch. Pharmacol. 179 (1973), R 13, one of the preferred compounds of BRD-OS 19 57 706 is 1-[2-(4-carbamoylphenoxy)-ethylamino]-3-(2-methylphenoxy)-propan-2-ol, Tolamol, a cardioselective $\beta$-receptor blocking agent. This compound, with an efficacy about equal to that of propranolol, nevertheless does not exhibit an "intrinsic sympathicomimetic activity".

The compounds of the instant invention are distinctly different from those of BRD-OS No. 19 57 706 in their different manner of activity.

The previously known amines with sympathicomimetic activity can be classified as either derivatives of phenylethylamines such as adrenaline, noradrenaline or dopamine, or derivatives of phenylisopropylamines such as pholedrin sulfate and oxyphedrine hydrochloride. All of these compounds exhibit a certain degree of α and/or $\beta$-adrenergic activity.

Therapeutic use of known sympathicomimetics in cardiocirculatory diseases, in particular cardiogenic shock, is subject to severe limitations due to the secondary effects upon the periphery of the cardiovascular system. Furthermore, the known sympathicomimetics all show cardiotoxic properties. As they cause a marked increase in heart frequency, this leads to increased demand for oxygen and substrates, and myocardiac necroses or disturbances of the tachycardiac rhythm may ensue.

Cardioselective sympathicomimetics, i.e. those acting specifically on $\beta$-receptors, have been to this time unknown.

DESCRIPTION OF THE INVENTION

The compounds of general formula I of the invention are highly efficacious, $\beta_1$-specific sympathicomimetics with a plurality antagonistic component. The pharmacological activity profile of these compounds is thus in distinct variance to the known sympathicomimetics as well as to the $\beta_1$-receptor blocking agents described in BRD-OS 19 57 706. In particular, pharmacological in vivo experiments have shown an increase in inotropy without a material increase in frequency within the μg/kg range (table 1). This is not the case with the compounds of BRD-OS No. 19 57 706, which exhibit an activity that is negative with respect to both inotropy and chronotropy.

The compounds of general formula I of the invention show novel cardiac effects, noted in more detail in Table 2. An increase in the contractive power of the heart is foremost. This is dependent upon dosage, the highest values being obtainable by varying the conditions of the experiment and the particular compounds used. A significant increase in cardiac frequency is noted only with a higher dosage, and the maximum increase in frequency is far below the increase in inotropy that can be achieved. There is no influence upon the arterial blood pressure and only a moderate resultant decrease in total peripheral pressure.

In contrast, the known $\beta$-sympathicomimetics such as d,1-oxyphedrine hydrochloride and isoprenaline induce increases in contractility, cardiac frequency and cardiac output, as well as a dilation of the peripheral cardiovascular system. These increases occur at approximately parallel rates. The very marked increase in frequency and cardiac output effort induce an excessive rise in the heart's oxygen demand. Dobutamine also causes a strong rise in inotropy; at higher dosages, this occurs concomitant with strong increases in frequency and in cardiovascular dilation. Moreover, the effective period of dobutamine is equal to the rather brief effective period of isoprenaline. Such cardiotoxic effects are absent in the compounds of the present invention.

$\beta$-adrenergic blocking can be demonstrated in in vitro experiments using a preparation of the isolated atrium cordis of the guinea pig. From Table 1, it can be seen that a number of the compounds exceed the efficacy of propranolol by several multiples. This adrenergic blockage is moreover of a high $\beta_1$-specificity; a blocking of $\beta_2$-receptors in the isolated trachea can be observed only with dosages which are higher by some three orders of magnitude.

The $\beta_1$-specific sympathicomimetics with a partially antagonistic component of the invention will increase the blood level of free fatty acids; however, dependent upon the dosage, they will concomitantly retard those increases induced by isoprenaline.

The selective action on the myocardium, accompanied by a reduced influence upon the chronotropy, can be ascribed to the distinctive balance achieved between sympathicomimetic activity and $\beta$-adrenergic blocking at the cardiac receptors. By virtue of their antagonistic component, these compounds will inhibit glycolysis in the myocardium, and thus lead to increases in myocardial glycogen. In contrast to isoprenaline, high dosages of the inventive compounds do not cause myocardial necroses. The arrhythmogenic effect of catecholamines is absent, and rhythmic disturbances such as caused by g-strophanthin are also subject to antagonistic control.

The invention makes available compounds with a wide therapeutic spectrum, due to the combination, hitherto unknown, of specific $\beta_1$-mimetic activity on the one hand, and antagonistic $\beta_1$-blocking activity when compared to certain cardiotoxic properties of known sympathicomimetics, on the other. Such agents can be used as cardiotonics for the treatment of acute and chronic cardiac insufficiencies. This is surprising, inasmuch as compounds of structure similar to general formula I had been recognized as structure-specific $\beta$-receptor blocking agents, but never before seen to exhibit such selective effects.

In Table 1, the results of tests comparing the inventive compounds with the prior art substances are recorded. $\beta$-adrenergic blockade in a preparation of isolated spontaneously beating atrium cordis of guinea pigs, compared with the positively inotropic effects of 0.015 $\mu$g/ml of isoprenaline, is given as the ED$_{50}$ in mol·10$^{-8}$. Also given in Table 1 are the results of determinations of $\beta$-mimetic effect on contractility and cardiac frequency in a marco-anesthetized cat treated with choralose-urethane. In this table, D is the dosage in mg/kg intravenous, HR is the percent change from the initial value in heart frequency, and dp/dt is the change in percent from the initial value in the maximum pressure increase rate in the left ventricle (dp/dt max). The last column shows the results of acute toxicity studies in rats, the LD$_{50}$ given in mg/kg intravenous.

TABLE 1

⟨⟩—O—CH$_2$—CH(OH)—CH$_2$—NH—CH$_2$—CH$_2$—NH—⟨A⟩

| components according to example | salt | A | ventricle ED$_{50}$ mol. 10$^{-8}$ | $\beta$-mimetic effect | | | LD$_{50}$ |
|---|---|---|---|---|---|---|---|
| | | | | D | HR | dp/dt | |
| 1 | HCl | 2-Cl | 5.49 | 0.01 | +11 | +59 | 21 |
| 7 | HCl | 2.6-CH$_3$ | 4.28 | 0.01 | +14 | +104 | 32 |
| 16 | HCl | 3-NO$_2$ | 2.20 | 0.01 | +13 | +57 | 44 |
| 17 | HCl | 3-NH$_2$ | 23.7 | 0.01 | +19 | +84 | 66 |
| Propranolol | HCl | — | 14.5 | 0.10 | −8 | −8 | 27 |
| d,l-oxyfedrin | HCl | — | 100 | 0.50 | +2 | +38 | 26 |
| Tolamolol | HCl | — | 5.52 | 0.10 | −10 | −17 | 133 |

Table 2 shows the effects of the inventive compounds and of prior art representatives on the circulation of dogs under continual intravenous infusion.

TABLE 2

| | 1 | 2 | | 3 | | 4 | | 5 | 6 | 7 |
|---|---|---|---|---|---|---|---|---|---|---|
| Compound as per Example | | | | | | | | | | |
| 1 | 1,00 | 30,0 | X | 3028–5326 | ED$_{30}$ = 11,0 | 80–107 | ED$_{30}$ = 20,0 | 115–195 | 111–113 | 7 |
| | | | % | +76 | Max = +91% | +34 | Max = +37% | +69 | +2 | |
| | | | P | 0,001 | at 50 | 0,02 | at 60 | 0,001 | ns | |
| 7 | 0,25 | 15,0 | X | 3834–6590 | ED$_{30}$ = 5,0 | 72–93 | ED$_{30}$ = 15,0 | 138–185 | 114–110 | 4 |
| | | | % | +72 | Max = +72% | +30 | Max = +30% | +35 | −3 | |
| | | | P | 0,01 | at 15 | ns | at 15 | ns | ns | |
| 16 | 1,00 | 10,0 | X | 3068–5230 | ED$_{30}$ = 5,0 | 83–94 | ED$_{30}$ = 20,0 | 129–169 | 103—103 | 7 |
| | | | % | +71 | Max = +100% | +13 | Max = +39% | +32 | ±0 | |
| | | | P | 0,005 | at 30 | ns | at 30 | 0,025 | ns | |
| 17 | 1,00 | 20,0 | X | 3071–5663 | ED$_{30}$ + 5,5 | 85–113 | ED$_{30}$ = 16,0 | 138–198 | 103–104 | 8 |
| | | | % | +84 | Max = +93% | +33 | Max = +49% | +44 | +1 | |
| | | | P | 0,01 | at 40 | 0,005 | at 50 | 0,025 | 0,45 | |
| Comparison Compound | | | | | | | | | | |
| Dobutamine | 12,5 | — | X | 3088–5410 | ED$_{30}$ = 7,5 | 78–84 | ED$_{30}$ = 23,0 | 152–186 | 101–103 | 4 |
| | | | % | +75 | Max = +191% | +8 | Max = +56% | +23 | +3 | |
| | | | P | 0,005 | at 50 | 0,15 | at 50 | 0,025 | 0,15 | |
| d-l-Oxyphedrine Hydrochloride | 10,0 | 200 | X | 3072–4600 | ED$_{30}$ = 130 | 75–117 | ED$_{30}$ = 130 | 112–186 | 106–93 | 8 |
| | | | % | +50 | Max = +89% | +56 | Max = +104% | +65 | −13 | |
| | | | P | 0,01 | at 500 | 0,001 | at 600 | 0,01 | 0,02 | |
| Iso-Prenaline-Sulphate | 0,125 | — | X | 3136–5140 | ED$_{30}$ = 0,038 | 76–115 | ED$_{30}$ = 0,06 | 130–253 | 116–113 | 9 |
| | | | % | +64 | Max = +116% | +51 | Max = +75% | +94 | −3 | |
| | | | P | 0,0005 | at 0,1875 | 0,0005 | at 0,1875 | 0,0005 | ns | |

This table may be interpreted as follows:

Column 1: Infusion rate in $\mu$g/kg/min
Column 2: Cumulative dose in $\mu$g/kg
Column 3:
  Rate of pressure increase in the left ventricle (dp/dt/max) in mm Hg·s$^{-1}$
  ED$_{30}$=dosage for 30% increase in inotropy, in $\mu$g/kg
  Max=maximum increase in percent in inotropy at dose $\mu$g/kg
Column 4: Cardiac frequency in n·min$^{-1}$
  ED$_{30}$=dosage for 30% increase in frequency, in $\mu$g/kg
  Max=maximum increase in percent in frequency at dose $\mu$g/kg
Column 5: Cardiac output ml·min$^{-1}$·kg$^{-1}$
Column 6: Diastolic blood pressure in mm Hg
Column 7: Number of animals used in the experiments
The other symbols in the table represent the following:
X=median values (initial value and after cumulative dose)
%=change in percent of initial value p=significance value
ns=not significant (p>0.05)
In these experiments, the compounds were used in the form of hydrochlorides.

The novel features which are considered as characteristic for the invention are set forth in particular in the appended claims. The invention itself, however, will be better understood from the following description of specific embodiments of the various synthetic routes for preparation of the compounds of the invention.

DESCRIPTION OF PREFERRED EMBODIMENTS

The inventive compounds may be prepared through a variety of synthetic routes. For example, one may synthesize the compounds of general formula I by reacting a diamine of the general formula:

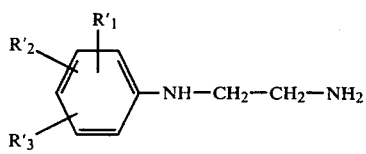

wherein $R_1'$, $R_2'$ and $R_3'$ either correspond to $R_1$, $R_2$ and $R_3$ in formula I or represent an amino group provided with a blocking or protective group, with a compound of the general formula:

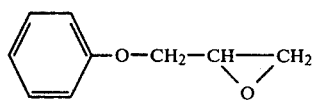

or

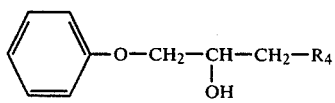

wherein $R_4$ is a halogen, such as bromine or chlorine, or a sulfonic acid residue, such as benzenesulfonyl or toluenesulfonyl, or a mixture of compounds III and IV. Reaction may be effected within the range from room temperature to the boiling point of the reactive mixture. At this point, any protective group present may be removed; in addition, nitro groups present may be reduced or amino groups acylated.

The reaction may be effected in the presence or absence of solvent. A preferred method proceeds in the presence of organic solvents; solvent with polar groups, such as lower alcohols, are particularly suitable, and of these, isopropanol is the solvent of choice.

With respect to this method and all following methods, protective groups that can be split off by hydrolysis or hydrogenolysis are particularly suitable for blocking the amino groups. Aliphatic or aromatic acyl residues, such as acetyl or benzoyl groups, or half esters of carbonic acid, such as alkoxy carbonyl groups, are examples of protective groups which can be removed by hydrolysis. Benzyl residues provide examples of protective groups amenable to hydrogenolysis.

The precursor diamines of general formula II can be produced by methods which are known per se. One method consists in the reaction with ammonia of compounds of the general formula:

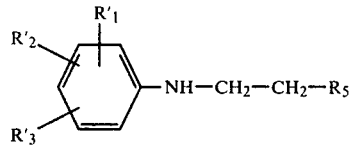

wherein $R_1'$, $R_2'$ and $R_3'$ are defined as above and $R_5$ is an exchangeable group such as halogen or sulfonyl residue, e.g. benzenesulfonyl and toluenesulfonyl. Other alternatives involve starting with compounds that may be converted into primary amines, such as potassium phthalimide, or reaction of appropriately substituted anilines with ethylenimine.

One may also synthesize the compounds of general formula I by converting 1-phenoxy-2,3-dibromopropane of the formula:

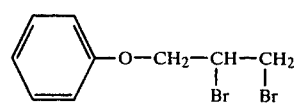

with a compound of general formula II in an inert organic solvent in the presence of a suitable base, such as triethylamine, into the aziridine derivative of the general formula:

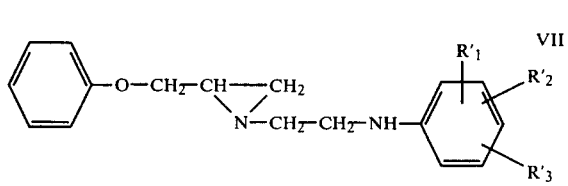

wherein $R_1'$, $R_2'$ and $R_3'$ are defined as above. Hydrolysis may be effected by heating in dilute mineral acid; protective groups may be removed, reduction of nitro groups and acylation of amino groups may also be effected, if desired.

The 1-phenoxy-2,3-dibromopropane of formula VI, used here as precursor, may be obtained in the manner known per se by bromination of phenyl allyl ether.

One may also produce compounds of general formula I by reaction of 2-hydroxy-3-phenoxy-propylamine of the formula:

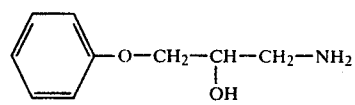

with a compound of general formula V, with the substituent groups defined as above. Removal of protecting groups, reduction of nitro groups and/or acylation of amino groups may follow as desired.

Another synthetic route to the compounds of general formula I is the reaction of compounds of the general formula:

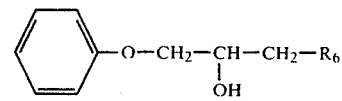

with another compound of the general formula:

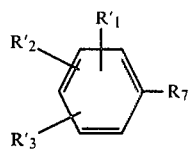

in the presence or absence of a solvent, and with use of a catalyst, such as ammonium chloride or $AlCl_3$. In these formulas, $R_1'$, $R_2'$ and $R_3'$ are as defined above; one of $R_6$ and $R_7$ is an aziridine group linked to the skeleton at the nitrogen atom, and the other residue is an amino group. These compounds may be produced by per se known methods. Again, removal of protective groups, reduction of nitro groups and/or acylation of amino groups may be effected as desired.

Insofar as compounds of the general formula I contain one or more nitro groups, these can be reduced to amino groups in the per se known manner.

If desired, the compounds of general formula I can be converted into the corresponding salts through addition with physiologically compatible inorganic or organic acids; conversely, the salts of the compounds can be converted, if desired, into free base form.

The methods of synthesizing these compounds of general formula I may be better understood through the following examples.

EXAMPLE 1

A solution of 11.2 g N-(2-chlorophenyl)-ethylenediamine and 9.9 g glycidphenyl ether in 50 ml isopropanol was heated to boiling for 5 hours. After cooling, the product which crystallized out was recovered by filtration, washed with ether and recrystallized from ethanol. A yield of 8.2 g was obtained of 3-[β-(2-chlorophenylamino)-ethyl]-amino-2-hydroxy-1-phenoxypropane, with a melting range 88°–91° C. Hydrogen chloride was introduced into a solution of this compound in 25 ml ethanol, and the hydrochloride precipitated by addition of 200 ml ether. After recrystallization from ethanol, 3-[β-(2-chlorophenylamino)-ethyl]-amino-2-hydroxy-1-phenoxypropane hydrochloride was obtained with a melting range of 126°–129° C.

EXAMPLE 2

By analogy to Example 1, reaction of 12.5 g of N-(4-chlorophenyl)-ethylenediamine and 11 g of glycidphenyl ether in 50 ml of isopropanol, yields 9.7 g (41.2% of theory) of 3-[β-(4-chlorophenylamino)-ethyl]-amino-2-hydroxy-1-phenoxypropane, with a melting range of 102°–104° C. The hydrochloride, prepared as in Example 1, showed a melting range of 178°–180° C.

EXAMPLE 3

A mixture of 30 g N-(2,6-dichlorophenyl)-ethylenediamine and 4.5 g glycidphenyl ether was heated for 10 hours at 120° C. After cooling, the mixture was diluted with 2 N hydrochloric acid until a pH value of 2 was obtained. The colorless precipitate was recovered by filtration, washed with water and recrystallized from ethanol. A yield of 7.5 g, 64% of theory based on the glycidphenyl ether, was obtained of 3-[β-(2,6-dichlorophenylamino)-ethyl]-amino-2-hydroxy-1-phenoxypropane hydrochloride, with a melting range between 149° and 153° C. The excess N-(2,6-dichlorophenyl)-ethylenediamine can be recovered by alkalizing the aqueous filtrate and extracting the compound with ether.

EXAMPLE 4

By analogy to Example 1, 14.1 g of N-(o-toluyl)-ethylenediamine and 14.1 g of glycidphenyl ether were reacted in 50 ml isopropanol. The solution was concentrated to dryness and the residue, which crystallized out after several days' standing, was washed with ether. The product 3-[β-(o-toluylamino)-ethyl]-amino-2-hydroxy-1-phenoxypropane, has a melting range between 69° and 73° C. The hydrochloride, prepared as in Example 1, has a melting range of 143°–144° C.

EXAMPLE 5

7.3 g of N-(m-toluyl)-ethylenediamine and 7.3 g glycidphenyl ether in 25 ml of isopropanol was heated to boiling for 5 hours, and the solution then concentrated to dryness. The viscous residue was subsequently dissolved in 20 ml ethanol, and hydrogen chloride introduced into the solution until complete precipitation was effected. After recrystallization from ethanol 6.2 g (37.6% of theory) of 3-[β-(m-toluylamino)-ethyl]-amino-2-hydroxy-1-phenoxypropane hydrochloride was isolated with a melting range 153°–157° C.

EXAMPLE 6

By analogy to Example 5, 8.2 g of N-(2,5-dimethylphenyl)-ethylenediamine and 7.5 g of glycidphenyl ether yielded 8.7 g (45% of theory) of 3-[β-(2,5-dimethylphenylamino)-ethyl]-amino-2-hydroxy-1-phenoxypropane dihydrochloride. Purification was effected by dissolving the compound in ethanol, boiling with activated carbon, filtration and precipitation with ether. The melting range was 138°–147° C.

EXAMPLE 7

As in Example 5, 16.4 g of N-(2,6-dimethylphenyl)-ethylenediamine and 15 g of glycidphenyl ether were reacted in 100 ml isopropanol and concentrated to dryness. Precipitation of the hydrochloride followed by introduction of hydrogen chloride into a solution of the above viscous residue in 100 ml ether. After several hours of standing, the crystallized 3-[β-(2,6-dimethylphenylamino)-ethyl]-amino-2-hydroxy-1-phenoxypropane hydrochloride was recrystallized from ethanol. Yield: 11.5 g (32.8% of theory); m.p.=168°–171° C.

EXAMPLE 8

Following Example 1, 10.2 g of N-(2,4-dichlorophenyl)-ethylenediamine was reacted with 7.5 of glycidphenyl ether. The crystallized product was dissolved in ethanol and hydrogen chloride introduced until an acid reaction was observed. Crystallization from this solution yielded 5.7 g (29.2% of theory) of 3-[β-(2,4-dichlorophenylamino)-ethyl]-amino-2-hydroxy-1-phenoxypropane hydrochloride with a melting point between 137° and 142° C.

EXAMPLE 9

As in Example 5, 9.2 g of N-(2-methyl-3-chlorophenyl)-ethylenediamine and 7.5 g glycidphenyl ether yielded 6 g (32.4% of theory) of 3-[β-(2-methyl-3-chlorophenylamino)-ethyl]-amino-2-hydroxy-1-phenoxypropane hydrochloride, with a melting range between 171° and 180° C.

EXAMPLE 10

As in Example 1, 12 g of N-(2,4,6-trichlorophenyl)-ethylenediamine and 7.5 g of glycidphenyl ether yielded 8.9 g (45.6% of theory) of 3-[β-(2,4,6-trichlorophenylamino)-ethyl]-amino-2-hydroxy-1-phenoxypropane, with a melting range 86°–89° C. The hydrochloride has a melting range 164°–166° C.

EXAMPLE 11

A solution of 3.7 g N-(2-bromo-4-methylphenyl)-ethylenediamine and 2.5 g glycidphenyl ether in 20 ml isopropanol was heated under reflux for 4 hours. After distillation of the isopropanol, a colorless oil remained which was dissolved in 50 ml chloroform. Hydrogen chloride was introduced into the solution until a pH of 6 was reached. After several days, the precipitated 3-[β-(2-bromo-4-methylphenylamino)-ethyl]-amino-2-hydroxy-1-phenoxypropane hydrochloride was recovered by filtration and recrystallized from 100 ml water. Yield: 2.5 g (37.3% of theory). Melting range: 132°–137° C.

EXAMPLE 12

A solution of 11 g N-(4-bromophenyl)-ethylenediamine and 7.5 g glycidphenyl ether in 55 ml isopropanol was left standing at room temperature for 16 hours. The colorless product crystallizing out after seeding was recovered by filtration and washed with isopropanol. A yield of 9.8 g of 3-[β-(4-bromophenylamino)-ethyl]-amino-2-hydroxy-1-phenoxypropane, 53.7% of theory, was obtained with a melting range between 106° and 110° C. The hydrochloride, obtained as in Example 5, has a melting range of 185°–187° C.

EXAMPLE 13

Analogous to Example 12, 10 g of N-(3-fluorophenyl)-ethylenediamine and 9.7 g glycidphenyl ether yielded 12.2 g (61.7% of theory) of 3-[β-(3-fluorophenylamino)-ethyl]-amino-2-hydroxy-1-phenoxypropane. Melting range: 107°–108° C. The hydrochloride, obtained as in Example 5, has a melting range of 151.5°–153° C.

EXAMPLE 14

By analogy to Example 1, 5.4 g of N-(4-nitrophenyl)-ethylenediamine and 4.5 g glycidphenyl ether in 25 ml isopropanol, yielded 6.35 g (64.5% of theory) of yellow 3-[β-(4-nitrophenylamino)-ethyl]-amino-2-hydroxy-1-phenoxypropane. The melting range was 131°–133° C. The hydrochloride produced in Example 5, has a melting range between 128°–132° C. and a yellow color.

EXAMPLE 15

As in Example 1, 5.6 g of N-(2-nitrophenyl)-ethylenediamine and 4.6 g glycidphenyl ether were used to prepare 7.1 g (70% of theory) of orange-colored 3-[β-(2-nitrophenylamino)-ethyl]-amino-2-hydroxy-1-phenoxypropane. M.p.=90°–95° C. The hydrochloride, produced according to Example 5, has a melting range of 156°–158° C. and a yellow color.

EXAMPLE 16

3.6 g of N-(3-nitrophenyl)-ethylenediamine, 3 g of glycidphenyl ether and 15 ml isopropanol were mixed together at room temperature. After standing for about an hour, a clear solution was obtained upon heating; after letting the solution stand overnight, a yellow product precipitated out of the solution. After recrystallization from ethanol the 3-[β-(3-nitrophenylamino)-ethyl]-amino-2-hydroxy-1-phenoxypropane obtained in this manner melted between 121° and 123° C. Yield: 4.1 g (62.9% of theory). A suspension of 4 g of this product in 50 ml water was heated to 90° C., and 2 N hydrochloric acid was added with stirring until a pH of 5 was reached. The hot solution was filtered through a frit and allowed to cool slowly after seeding. The 3-[β-(3-nitrophenylamino)-ethyl]-amino-2-hydroxy-1-phenoxypropane hydrochloride was filtered off and dried at 100° C. The melting range of the product was 159°–161° C.

Hydrobromide: m.p.=139°–143° C.

Hemisulfate: m.p.=182°–185° C.

EXAMPLE 17

4 g of 3-[β-(3-nitrophenylamino)-ethyl]-amino-2-hydroxy-1-phenoxypropane in 60 ml methanol was heated for 16 hours at 80° C. in an autoclave at a hydrogen pressure of 60 atmospheres and in the presence of 5 g Raney nickel catalyst. The catalyst was then removed by filtration; the filtrate was concentrated to 20 ml, diluted with 20 ml acetone, and hydrogen chloride introduced until complete precipitation occurred. After filtration and washing of the residue with acetone, the product was dried at room temperature. A yield of 2.68 g (53.6% of theory) of 3-[β-(3-aminophenylamino)-ethyl]-amino-2-hydroxy-1-phenoxypropane trihydrochloride was obtained; the product decomposes between 160° and 170° C.

EXAMPLE 18

Analogous to Example 12, 8.3 g N-(4-methoxyphenyl)ethylenediamine and 7.5 g glycidphenyl ether yielded 7.8 g (49.4%) of 3-[β-(4-methoxyphenylamino)-ethyl]-amino-2-hydroxy-1-phenoxypropane. Melting point between 112° and 114° C. The hydrochloride produced as in Example 5 has a melting range between 183°–185° C.

EXAMPLE 19

Analogous to Example 1, 11.1 g N-phenylethylenediamine and 12.2 g glycidphenyl ether in 70 ml isopropanol yielded 9.3 g (39.8%) of 3-(β-phenylaminoethyl)-amino-2-hydroxy-1-phenoxy propane with a melting point between 109° and 113° C. The 3-(β-phenylaminoethyl)-amino-2-hydroxy-1-phenoxypropane dihydrochloride was obtained by dissolving the free base in ethanol and introducing hydrogen chloride; upon recrystallization from ethanol, it shows a melting range of 145°–153° C.

EXAMPLE 20

A mixture of 30 g N-(2,6-dichlorophenyl)-ethylenediamine and 9.3 g 3-chloro-2-hydroxy-1-phenoxypropane was heated for 10 hours at 120° C. After cooling, 50 ml 2 N hydrochloric acid was added, the product filtered out, and washed with water and ethanol. After drying, the yield was 13.6 g (about 69.4% of theory based on 3-chloro-2-hydroxy-1-phenoxypropane) of 3-[β-(2,6-dichlorophenylamino)-ethyl]-amino-2-hydroxy-1-phenoxypropane hydrochloride with a melting range between 145° and 148° C. The excess N-(2,6-dichlorophenyl)-ethylenediamine can be recovered by the method described in Example 3.

EXAMPLE 21

A mixture of 5 g 3-amino-2-hydroxy-1-phenoxypropane and 6.7 g N-(β-chloroethyl)-2,6-dichloroaniline was heated for 8 hours at 120° C. to 140° C. 25 ml of 2 N hydrochloric acid was added to the still-warm melt. The precipitate was recovered by filtration and recrystallized from ethanol. A yield of 3.4 g (28.9%) of 3-[β-(2,6-dichlorophenylamino)-ethyl]-amino-2-hydroxy-1-phenoxy propane hydrochloride was obtained, with a melting point between 139° and 148° C.

EXAMPLE 22

A solution of 14 g 1-(2-hydroxy-3-phenoxypropyl)aziridine in 20 ml toluene was added dropwise to a suspension of 12.6 g 4-bromoaniline and 9.7 g anhydrous aluminum chloride in 35 ml toluene at 90° C. Stirring was maintained at 90° C. for 90 minutes. After cooling, 90 ml of 30% sodium hydroxide solution was added dropwise, the cooled mixture filtered through a frit and the residue washed with water and toluene. After recrystallization of the residue from ethanol, a yield of 4.9 g (18.4% of theory) of 3-[β-(4-bromophenylamino)-ethyl]-amino-2-hydroxy-1-phenoxypropane was obtained, with a melting point of 106°-110° C.

Without further analysis, the foregoing will so fully reveal the gist of the present invention that others by applying current knowledge can readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A compound of the general formula:

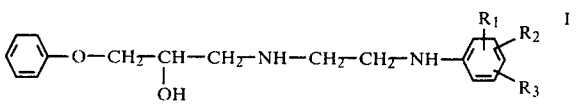

and salts thereof with physiologically compatible inorganic or organic acids, wherein $R_1$, $R_2$ and $R_3$ are the same or different and are hydrogen, alkyl of 1 to 2 C atoms, methoxy, halogen, amino, nitro or acylamino residues.

2. A compound as defined in claim 1, which is 3-[β-(2-chlorophenylamino)-ethyl]-amino-2-hydroxy-1-phenoxypropane.

3. A compound as defined in claim 1, which is 3-[β-(4-chlorophenylamino)-ethyl]-amino-2-hydroxy-1-phenoxypropane.

4. A compound as defined in claim 1, which is 3-[β-(2,6-dichlorophenylamino)-ethyl]-amino-2-hydroxy-1-phenoxypropane.

5. A compound as defined in claim 1, which is 3-[β-(o-toluylamino)-ethyl]-amino-2-hydroxy-1-phenoxypropane.

6. A compound as defined in claim 1, which is 3-[β-(m-toluylamino)-ethyl]-amino-2-hydroxy-1-phenoxypropane.

7. A compound as defined in claim 1, which is 3-[β-(2,5-dimethylphenylamino)-ethyl]-amino-2-hydroxy-1-phenoxypropane.

8. A compound as defined in claim 1, which is 3-[β-(2,6-dimethylphenylamino)-ethyl]-amino-2-hydroxy-1-phenoxypropane.

9. A compound as defined in claim 1, which is 3-[β-(2,4-dichlorophenylamino)-ethyl]-amino-2-hydroxy-1-phenoxypropane.

10. A compound as defined in claim 1, which is 3-[β-(2-methyl-3-chlorophenylamino)-ethyl]-amino-2-hydroxy-1-phenoxypropane.

11. A compound as defined in claim 1, which is 3-[β-(2,4,6-trichlorophenylamino)-ethyl]-amino-2-hydroxy-1-phenoxypropane.

12. A compound as defined in claim 1, which is 3-[β-(2-bromo-4-methylphenylamino)-ethyl]-amino-2-hydroxy-1-phenoxypropane.

13. A compound as defined in claim 1, which is 3-[β-(4-bromophenylamino)-ethyl]-amino-2-hydroxy-1-phenoxypropane.

14. A compound as defined in claim 1, which is 3-[β-(3-fluorophenylamino)-ethyl]-amino-2-hydroxy-1-phenoxypropane.

15. A compound as defined in claim 1, which is 3-[β-(4-nitrophenylamino)-ethyl]-amino-2-hydroxy-1-phenoxypropane.

16. A compound as defined in claim 1, which is 3-[β-(2-nitrophenylamino)-ethyl]-amino-2-hydroxy-1-phenoxypropane.

17. A compound as defined in claim 1, which is 3-[β-(3-nitrophenylamino)-ethyl]-amino-2-hydroxy-1-phenoxypropane.

18. A compound as defined in claim 1, which is 3-[β-(3-aminophenylamino)-ethyl]-amino-2-hydroxy-1-phenoxypropane.

19. A compound as defined in claim 1, which is 3-[β-(4-methoxyphenylamino)-ethyl]-amino-2-hydroxy-1-phenoxypropane.

20. A compound as defined in claim 1, which is 3-[β-(3-acetylaminophenyl-amino)-ethyl]-amino-2-hydroxy-1-phenoxypropane.

* * * * *